United States Patent
Feng et al.

(10) Patent No.: US 9,631,221 B1
(45) Date of Patent: Apr. 25, 2017

(54) IDENTIFICATION OF MICROORGANISMS USING MALDI-TOF-MS ON-PLATE EXTRACTION

(75) Inventors: Liping Feng, Baltimore, MD (US); William B. Brasso, Columbia, MD (US); Susan M. Kircher, Hanover, PA (US); Vanda White, Baltimore, MD (US); Song Shi, Reisterstown, MD (US); Xiao Mo, Ellicott City, MD (US); Tuan-Linh Ngoc Nguyen, Carlisle, PA (US); Adrien Malick, Sparks, MD (US); Jon E. Salomon, Stewartstown, PA (US); John D. Mantlo, Sykesville, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 50 days.

(21) Appl. No.: 13/600,702

(22) Filed: Aug. 31, 2012

Related U.S. Application Data

(60) Provisional application No. 61/530,620, filed on Sep. 2, 2011, provisional application No. 61/649,483, filed on May 21, 2012.

(51) Int. Cl.
  *C12Q 1/04* (2006.01)
  *G01N 33/68* (2006.01)

(52) U.S. Cl.
  CPC .......... *C12Q 1/04* (2013.01); *G01N 33/6851* (2013.01)

(58) Field of Classification Search
  None
  See application file for complete search history.

(56) References Cited

U.S. PATENT DOCUMENTS

2006/0269564 A1* 11/2006 Emery et al. .............. 424/190.1
2010/0120085 A1    5/2010 Hyman et al.

FOREIGN PATENT DOCUMENTS

| JP | 2011174887 A | 9/2011 |
| WO | 2010100612 A1 | 9/2010 |
| WO | 2011006911 A2 | 1/2011 |
| WO | 2012016929 A1 | 2/2012 |

OTHER PUBLICATIONS

Madonna et al., On-probe sample pretreatment for the detection of proteins above 15 KDa from whole cell bacteria by matrix-assisted laser desorption/ionization time-of-flight mass spectrometry, Rapid Communications in Mass Spectrometry, (2000) 14, 2220-2229.*
Bizzini et al., "Performance of matrix-assisted laser desorption Ionization-time of flight mass spectrometry for identification of bacterial strains routinely isolated in a clinical microbiology laboratory", Journal of Clinical Microbiology, May 2010, pp. 1549-1554.
Haigh et al., Journal of Clinical Microbiology, Jul. 6, 2001.
Herendael et al., "Validation of a modified algorithim for the identification of yeast isolates using matrix-assisted laser desorption/ionisation time-of-flight mass spectrometry (MALDI-TOF-MS)", Eur J. Clin Microbiol Infect Dis, 2011.
Schmidt et al., "Rapid identification of bacteria in positive blood culture by matrix-assisted laser desorption ionization time-of-fligt mass spectrometry", Eur J. Clin Microbiol Infect Dis, 2011.

* cited by examiner

*Primary Examiner* — Karen Cochrane Carlson
*Assistant Examiner* — Jennifer M. H. Tichy
(74) *Attorney, Agent, or Firm* — Lerner, David, Littenberg, Krumholz & Mentlik, LLP

(57) ABSTRACT

Rapid methods that identify sepsis-causing bacteria or yeast aid the physician in critical therapeutic decision-making, thus decreasing patient mortality rates. The methods described herein employ plating microorganisms directly on to a MALDI-MS plate, adding concentrated formic acid, and identifying the microorganism by mass spectrometry. Optionally, an organic solvent may be combined with the formic acid, or added to the sample before or after the concentrated formic acid is added thereto. The methods enable direct extraction of proteins from microorganisms without the need for liquid protein extraction methods and yields positive identification results for gram-positive bacteria, gram-negative bacteria and yeast in minutes.

12 Claims, 3 Drawing Sheets

IDENTIFICATION OF MICROORGANISMS USING MALDI-TOF-MS ON-PLATE EXTRACTION

CROSS REFERENCE TO RELATED APPLICATIONS

This application claims the benefit of the filing date of U.S. Provisional Patent Application No. 61/649,483 filed May 21, 2012 and U.S. Provisional Patent Application No. 61/530,620 filed Sep. 2, 2011, the disclosures of which are hereby incorporated herein by reference.

BACKGROUND OF THE INVENTION

Sepsis is a serious medical condition caused by an overwhelming response of the host immune system to infection. It can trigger widespread inflammation, which can give rise to impaired blood flow. As sepsis progresses, the body's organs can be starved for oxygen and nutrients, causing permanent damage and eventual failure. Left improperly diagnosed or otherwise untreated, the heart weakens and septic shock can occur, leading to multiple organ failure and death. Blood cultures are required to detect the presence of bacteria or yeast in the blood of sepsis patients, to identify the microorganism(s) present and guide treatment. The conventional separation and identification of microorganism(s) from blood cultures takes at least 24-48 hours, which results in many of the septicemia patients being initially treated with inappropriate antibiotics. It is therefore desirable to separate and identify microorganisms from a positive culture (blood, cerebrospinal fluid etc.) rapidly.

Recently, certain proteomic technologies/tools, such as Matrix-Assisted Laser Desorption Ionization Time of Flight mass spectrometry, ("MALDI-TOF MS"), have been shown to provide a rapid and accurate identification of bacteria and/or fungi from a positive blood culture ("PBC"). The microorganism in the PBC sample can be sub-cultured prior to MALDI identification. In the alternative, microorganisms can be isolated from the PBC sample using various sample preparation methods without the need for subculturing. The microorganism isolates are generally directly smeared onto a MALDI plate to yield about 70-80% identification accuracy. For isolates failing to yield any identification, a follow-up liquid extraction method is typically used to extract proteins from the microorganism for improved identification by MALDI-TOF MS. Although these liquid protein extraction methods generally yield better identification accuracy, such methods not only require several centrifugation steps, but also are time-consuming.

Schmidt et al (Rapid identification of bacteria in positive blood culture by matrix-assisted laser desorption ionization time-of-flight mass spectrometry, *Eur. J. Clin. Microbiol. Infect Dis*, 23 Jun. 2011) discloses a method of identifying bacteria from positive blood cultures by spotting a liquid sample of the isolated bacteria onto a MALDI plate and overlaying 25% formic acid directly to the spotted liquid sample. Therefore, the final concentration of formic acid in the bacterial sample is less than 25%. The Schmidt method results in 86.6% identification accuracy for gram-negative bacteria and 60% identification accuracy for gram-positive bacteria. Schmidt does not test this method in Yeast.

Hyman et al (U.S. Patent Publication No. 2010/0120085, Published May 13, 2010), discloses a similar method as Schmidt, in which intact isolated microorganisms in solution are directly smeared onto a MALDI plate. The liquid sample is then overlaid with roughly an equal volume of 50% formic acid. Therefore, the final concentration of formic acid added to the sample is approximately 25%. This method was tested on 14 different species of bacteria and yeast. Although this method resulted in 91.1% identification, the data does not indicate how effective this method is with regard to gram-positive bacteria, gram-negative bacteria, or yeast.

Haigh et al. "Improved Performance of Bacterium and Yeast Identification by a Commercial Matrix-Assisted Laser Desorption Ionisation-Time of Flight Mass Spectrometry System in the Clinical Microbiology Laboratory, "*J. Clin. Microbiol.* (Jul. 6, 2011) describes a method in which neat formic acid is used to extract microbial proteins smeared directly onto a MALDI plate. This method, however, was unable to successfully identify all strains of yeast and gram-positive bacteria.

Herendael et al. "Validation of a modified algorithm for the identification of yeast isolates using matrix-assisted laser desorption/ionisation time-of-flight mass spectrometry (MALDI-TOF MS)", *Eur. J. Clin. Microbiol. Infect Dis* (23 Aug. 2011) describes two methods for the identification of yeast. The standard extraction method described in Herendael et al., is a conventional liquid extraction method (this method is the "prior art procedure" of Example 1 hereinbelow). In the short extraction method described in Herendael et al., one colony was picked from an agar plate and applied directly to the target MALDI plate. Formic acid (1 µL at 70% concentration) was added to the sample and the sample was allowed to dry. The dried sample was overlaid with MALDI matrix, allowed to dry further, and analyzed by MALDI-MS. The short extraction method provided identical results as the standard extraction method although the MALDI scores were lower with the short extraction method. Nearly all of the isolates (97.6%) could be identified with the short extraction method; however 17.1% of these identifications fell below the reliable threshold level of 1.7.

Accordingly, there is a need to develop a rapid and accurate method of identifying all classes of bacteria and yeast without the need for liquid protein extraction prior to identification with MALDI-TOF MS.

SUMMARY OF THE INVENTION

Various embodiments of the disclosed method enable direct identification of microorganisms from positive blood cultures ("PBC") or pure isolates by mass spectrometry without the need for a liquid protein extraction. In one embodiment of this method, identification of a microorganism from a pure isolate is achieved by obtaining a sample containing at least one microorganism, depositing at least a portion of the pure isolate sample (direct smear or microbial suspension) on a solid surface adapted to be placed in an apparatus configured to determine the identity of microorganisms by MALDI mass spectrometry, treating the sample with a volatile acid, an organic solvent, and/or a combination of organic solvent and a volatile acid, drying the sample, placing a MALDI matrix solution over the treated sample, and identifying the microorganism by MALDI mass spectrometry.

Optionally, a PBC sample is first processed to isolate the microorganism, followed by identification of the microorganism without performing a liquid protein extraction. This embodiment is achieved by: i) obtaining a PBC sample determined to contain at least one microorganism; ii) adding a lysis buffer to the sample to lyse the blood cells; iii) while the microorganism remains intact and viable, isolating the intact microorganism; iv) depositing the isolated microorganism on a solid surface adapted to be placed in an apparatus configured to determine the identity of microorganisms by MALDI mass spectrometry; v) treating the sample with a volatile acid, an organic solvent, and/or a combination of organic solvent and a volatile acid; vi) placing a MALDI matrix solution over the treated sample; and vii) identifying the microorganism by mass spectrometry. In another embodiment, the PBC sample is sub-cultured to produce a pure culture of the microorganism prior to identifying the microorganism. In one embodiment, the sample can be dried before treating the sample with a volatile acid, an organic solvent, and/or a combination of organic solvent and a volatile acid; placing a MALDI matrix solution over the treated sample; and/or identifying the microorganism by mass spectrometry (i.e., before the treating step v) above).

The described methods can be used to isolate and/or identify a spectrum of microorganisms including but not limited to, gram-positive bacteria, gram-negative bacteria, fungi, mycobacterium, or yeast.

In another embodiment, a kit is provided for the detection of microorganisms in a sample. The kit includes, for example, one or more of the reagents and/or buffers described herein for processing a sample known to contain at least one microorganism for downstream identification.

DETAILED DESCRIPTION

Figure 1:
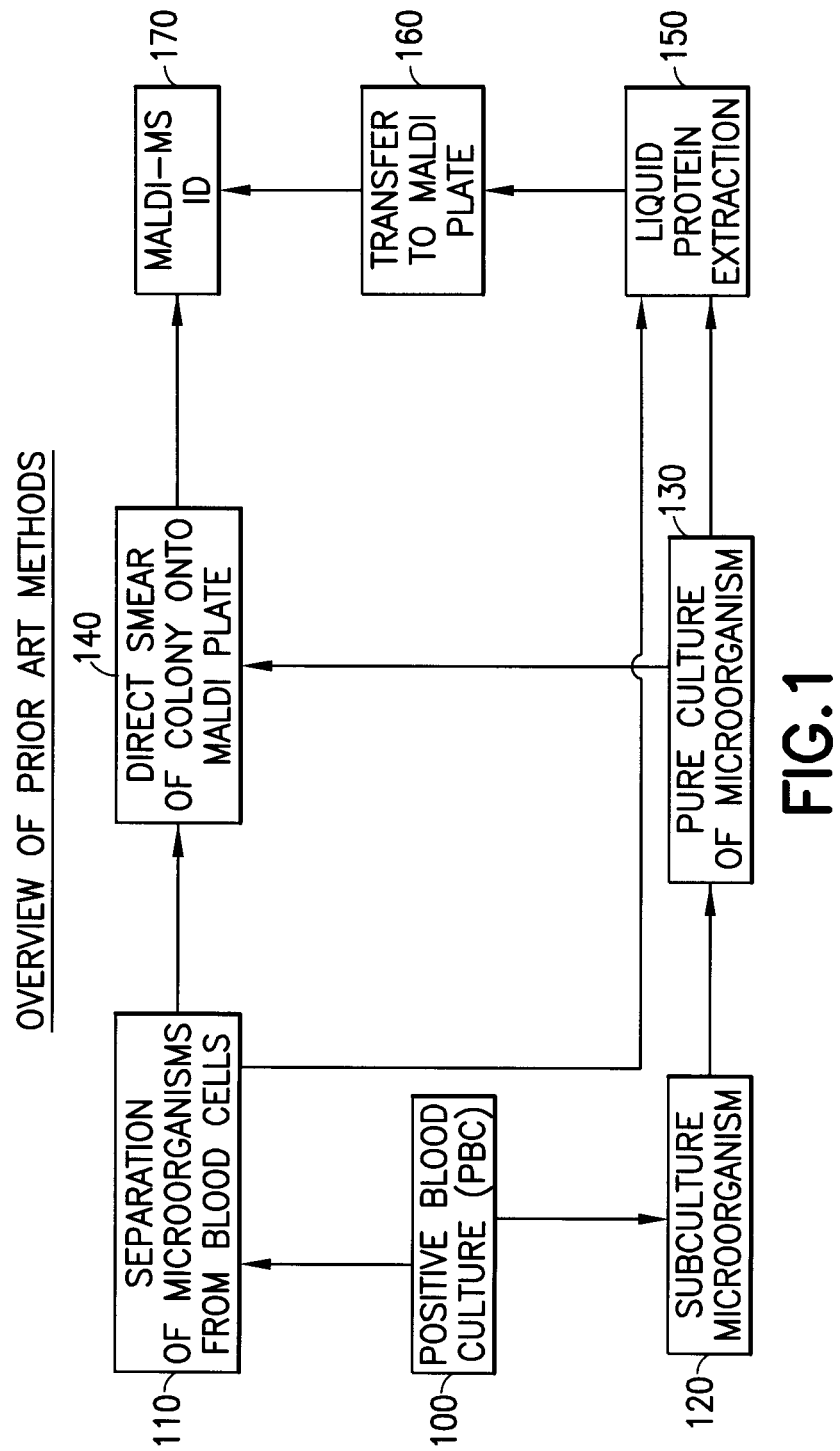
FIG. 1 is a flowchart that illustrates the prior art method of extracting proteins from pure microbial isolates for identification by mass spectrometry.

FIG. 1 illustrates the prior art methods of identifying microorganisms from PBC. These methods are known to one having ordinary skill in the art. For example, these methods are described in Nassiff et al WO 2010/100612 A1, the disclosure of which is incorporated herein by reference. A positive blood culture 100 is obtained. The microorganism is isolated from the remaining blood cells and debris either by liquid separation 110 or by sub-culturing the microorganism 120 to produce a pure culture of microorganism 130. To identify the microorganism, microorganism separated by liquid separation 110 or the pure culture 130 can be directly smeared onto a MALDI plate 140 for MALDI-MS identification 170 or undergo liquid protein extraction 150 prior to transferring to the MALDI plate 160 and identification by MALDI-MS 170.

In one embodiment of the invention, direct identification of microorganisms is achieved from pure isolates or a PBC sample by mass spectrometry without requiring a liquid protein extraction. In one embodiment, the microorganism from pure isolates is identified by: i) obtaining a sample suspected to contain at least one microorganism; ii) depositing at least a portion of the sample on a solid surface adapted to be placed in an apparatus configured to determine the identity of microorganisms by MALDI mass spectrometry in a manner that controls any dilution of a volatile acid and/or an organic solvent to be combined with the deposited sample; iii) treating the sample with at least one reagent; such reagents including a volatile acid, an organic solvent, and/or a combination of organic solvent and a volatile acid; iv) placing a MALDI matrix solution over the treated sample; and v) identifying the microorganism by mass spectrometry. In one embodiment the volatile acid is at least 70% formic acid. In another embodiment the volatile acid is at least 80% formic acid. In another embodiment the volatile acid is at least 90% formic acid. Unless otherwise specified herein, the formic acid solutions are aqueous solutions. In another embodiment the volatile acid is at least 100% formic acid (e.g. neat). In another embodiment, the sample is treated with at least 70% formic acid in an organic solvent such as acetonitrile, methanol, ethanol, acetone, or ethyl acetate prior to placing a MALDI matrix solution over the sample. In another embodiment, the sample is treated with at least 80% formic acid in an organic solvent such as acetonitrile, methanol, ethanol, acetone, or ethyl acetate prior to placing a MALDI matrix solution over the sample. In another embodiment, the sample is treated with at least 90% formic acid in an organic solvent such as acetonitrile, methanol, ethanol, acetone, or ethyl acetate prior to placing a MALDI matrix solution over the sample. In one embodiment, the sample deposited on the solid surface is allowed to dry prior to adding the volatile acid, to prevent the sample from diluting the volatile acid. In another embodiment, the volatile acid is dried prior to placing the MALDI matrix solution over the sample. Examples of the volatile acids that may be used in the various embodiments of the invention include, but are not limited to, formic acid, acetic acid, trifluoracetic acid and hydrochloric acid. In another embodiment, a kit is provided comprising one or more of the reagents and/or buffers described herein for processing a sample known to contain at least one microorganism for downstream identification.

In another embodiment, the disclosed methods are used to isolate and/or identify gram-positive bacteria, gram-negative bacteria, or yeast. In another embodiment, the disclosed methods are used to isolate and/or identify *Streptococcus pneumoniae*. In another embodiment, the disclosed methods are used to isolate and/or identify yeast, including *Cryptococcus neoformans*.

In one embodiment, identification of microorganisms having thickened or hydrophobic cell wall complexes, for example, yeast and mycobacteria, is performed by using any of the methods described herein, which deploy an organic solvent, among other reagents, for on-plate extraction. In a preferred embodiment, *Cryptococcus neoformans* is the microorganism targeted for identification. Without being bound by a particular theory, it is believed that the organic solvent dissolves or disperses interfering substances in the cell wall and/or bound extracellular material, such as polysaccharides or lipids, and makes the cell wall and intracellular proteins more susceptible and more accessible, respectively, to the extraction methods.

After the sample is combined with the reagent(s), the combination of sample and reagents is dried. Drying is defined as allowing the liquid to evaporate sufficiently so as not to dilute any liquid subsequently added. While the sample can be dried in ambient air, a heating source, such as a heating block, hot plate, heating oven or infrared heating lamp can be used to accelerate the evaporation of the liquid portion of the combined sample and reagents. These drying methods do not change the spectrum of the sample upon identification by MALDI.

After the extracted sample is dried, it is combined with additional reagents for downstream sample assay using MALDI. Any MALDI matrix solution known to those skilled in the art can be used in the disclosed methods. These matrix solutions include, but are not limited to, α-cyano-4-hydroxycinnamic acid (HCCA), 2,5-dihydroxybenzoic acid (DHB), 3,5-dimethoxy-4-hydroxycinnamic acid (SPA), 3-hydroxypicolinic acid (HPA), 3.4-dihydroxycinnamic acid, 2-(4-hydroxyphenylazo)-benzoic acid, 2-amino-4-methyl-5-nitropyridine, and 2,4,6-trihydroxy acetophonone (THAP).

In one embodiment, the methods described herein can also include using a non-ionic detergent capable of solubilizing proteins as an extraction reagent in addition to those described above. The detergent does not interfere with the MALDI ionization process. These detergents can be incorporated into the initial microorganism suspension or subsequent volatile acid and/or organic solvent treatment. Typical detergents suitable for MALDI include, for example, n-octyl-β-D-glucopyranoside (OG), saponin, triton, and those described in International Publication No. WO 2010/100612, incorporated herein by reference. In one embodiment, the concentration of detergent is in the range of 1% to 5%. In another embodiment, the concentration of detergent is 2%.

Figure 2:
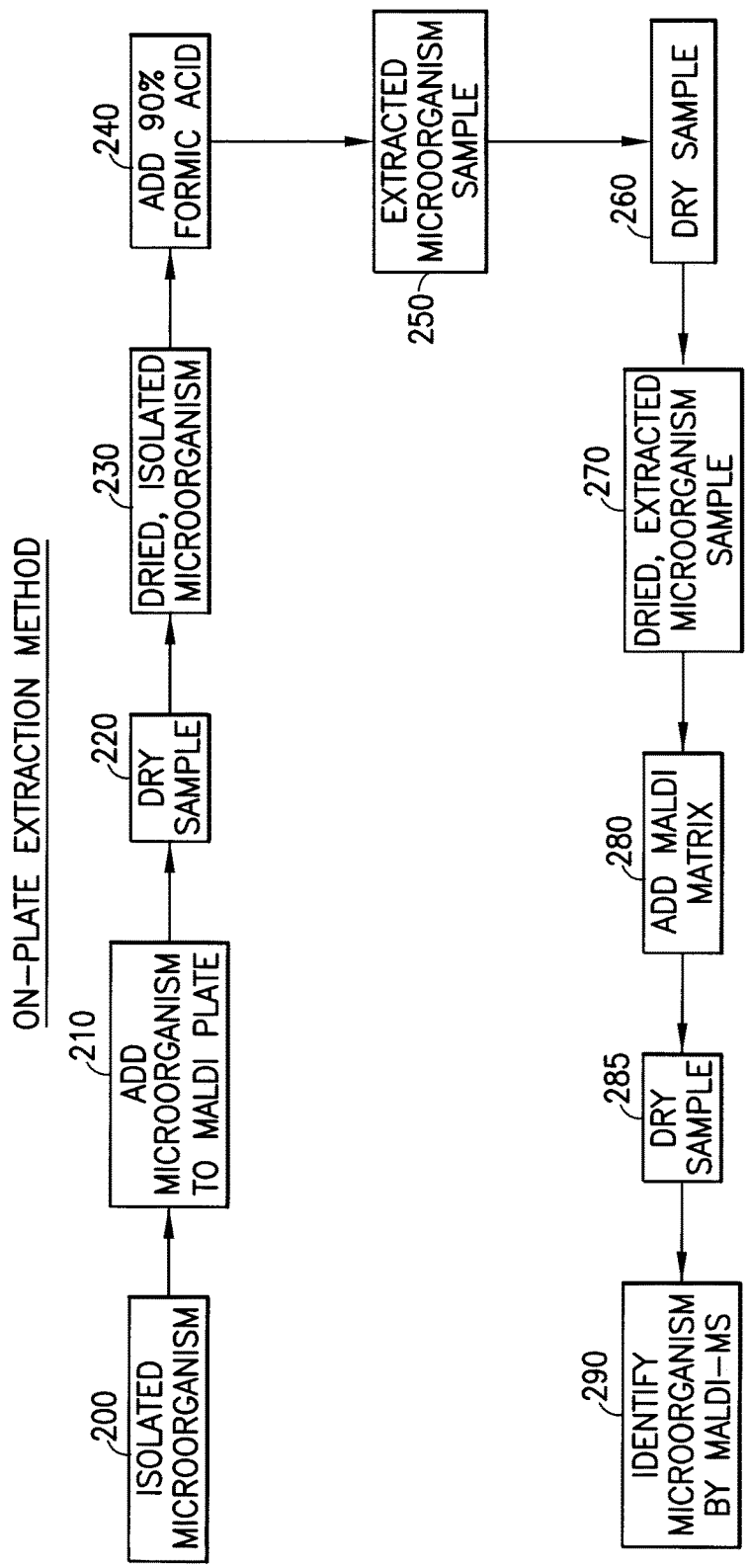
FIG. 2 illustrates one embodiment of the disclosed method in which proteins are extracted from isolated microorganisms directly on a MALDI plate using concentrated formic acid.

Referring to FIG. 2, which illustrates the protein extraction method of one embodiment of the disclosed methods, an isolated microorganism 200 is obtained (i.e. pure culture from sub-culturing or liquid separation as described in FIG. 1). The isolated microorganism 200 is added directly to the MALDI plate 210. The isolated microorganism 200 on MALDI plate 210 is allowed to air dry 220 to produce dried, isolated microorganism 230. Ninety percent formic acid 240 is applied to the dried, isolated microorganism sample 230 to obtain extracted microorganism sample 250 which contains solubilized proteins of the microorganism. Extracted microorganism sample 250 is allowed to air dry 260 to produce dried, extracted microorganism sample 270. MALDI matrix 280 is added to dried, extracted microorganism 270, allowed to air dry 285, and identified by MALDI-MS 290.

In another embodiment, the microorganism is identified by: i) obtaining a sample suspected of containing at least one microorganism; ii) depositing by direct smear at least a portion of the sample on a solid surface adapted to be placed in an apparatus configured to determine the identity of microorganisms by MALDI mass spectrometry; iii) drying the sample; iv) treating the sample with at least 70% formic acid in an aqueous solution or at least 70% formic acid in an organic solvent; v) drying the sample; vi) placing a MALDI matrix solution over the treated sample; vii) drying the sample; and viii) identifying the microorganism by mass spectrometry. In another embodiment, a kit is provided comprising one or more of the reagents and/or buffers described herein for processing a sample known to contain at least one microorganism for downstream identification.

In yet another embodiment, the microorganism is identified by: i) obtaining a sample suspected of containing at least one microorganism; ii) depositing by direct smear at least a portion of the sample on a solid surface adapted to be placed in an apparatus configured to determine the identity of microorganisms by MALDI mass spectrometry; iii) treating the sample with an organic solvent; iv) drying the sample; vii) treating the sample with formic acid and an organic solvent; v) drying the sample; vi) placing a MALDI matrix solution over the treated sample; vii) drying the sample; and viii) identifying the microorganism by mass spectrometry. In one embodiment, the organic solvent is ethanol, methanol, isopropanol, or acetone. In another embodiment, a kit is provided comprising one or more of the reagents and/or buffers described herein for processing a sample known to contain at least one microorganism for downstream identification.

In yet another embodiment, the sample suspected of containing at least one microorganism is resuspended in a solution prior to deposition onto the solid surface adapted to be placed in an apparatus configured to determine the identity of microorganisms by MALDI mass spectrometry. One skilled in the art will appreciate that the concentration of the microbial suspension will be optimized for the various disclosed embodiments. For example, in one embodiment, a higher concentration of microbial suspension may be required, such as a concentration greater than 0.5 McFarland (for example, about 0.75 McFarland and higher), to better ensure proper identification of the microorganism (or a reliable indication of the absence of the microorganism) by MALDI-MS. In another embodiment, the concentration of the microbial suspension can be adjusted for use in the various disclosed embodiments as well as in additional assays, such as those described in U.S. patent application Ser. No. 13/177,031 (which is incorporated by reference herein), which include, for example, antimicrobial susceptibility testing (AST). In one embodiment, the microbial suspension is at least about 2.0 McFarland or higher.

One skilled in the art is aware that MALDI identification results are affected by the amount of cells deposited onto the MALDI plate. A standardized microbial suspension provides a uniform dispersion of cells, leading to more precise and reproducible results. In one embodiment, the microbial suspension is standardized prior to deposition onto the solid surface adapted to be placed in an apparatus configured to determine the identity of microorganisms by MALDI mass spectrometry. The microbial suspension can be optionally adjusted to a certain McFarland standard. Creation of the standardized microbial suspension can be accomplished by various methods well known to those skilled in the art, for example, using an inoculation loop, microdropper, or other physical methods. In a preferred embodiment, a microbial suspension is adjusted to a McFarland standard of at least 0.5 prior to deposition onto a MALDI plate. In another embodiment, a microbial suspension is adjusted to a McFarland standard in the range of 0.5-10 McFarland prior to deposition onto a MALDI plate.

Figure 3:
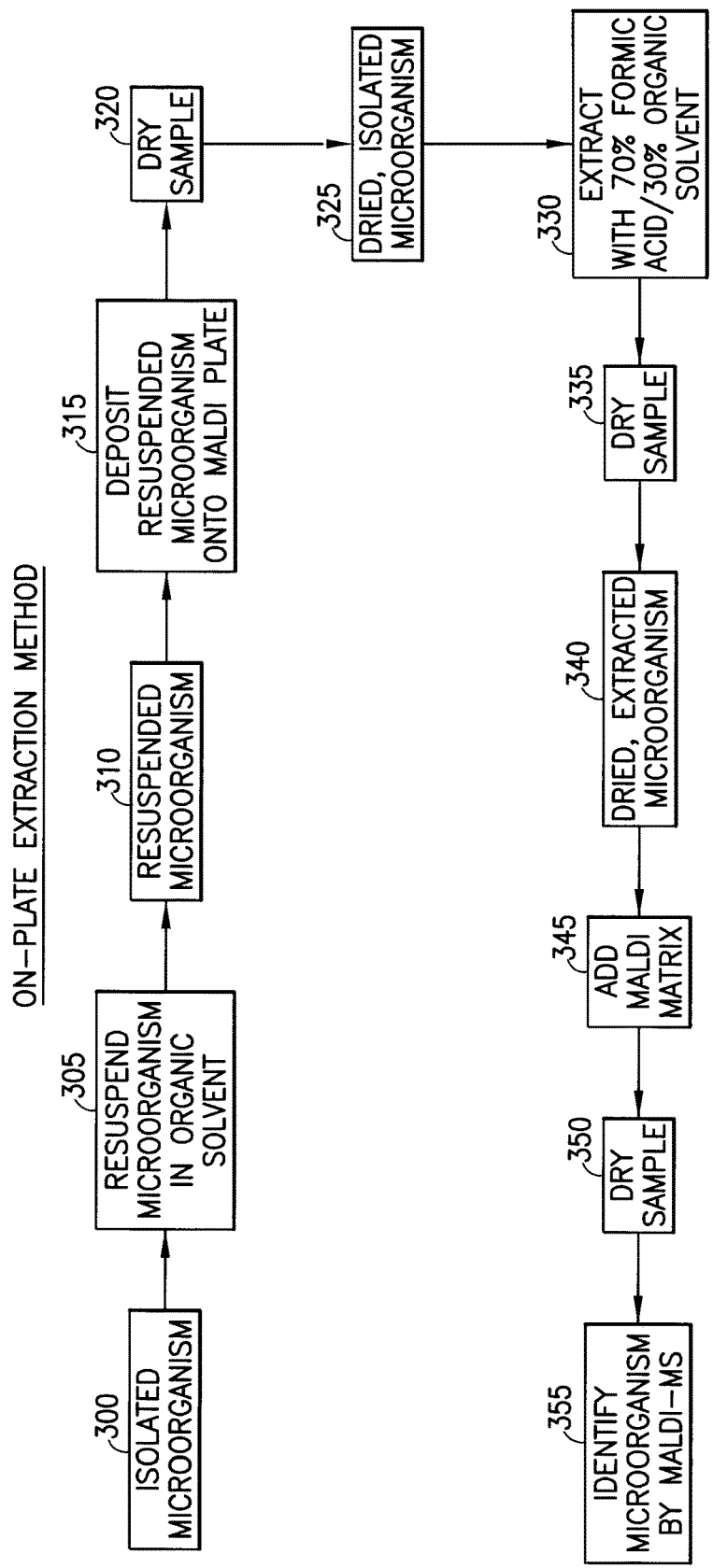
FIG. 3 illustrates one embodiment of the disclosed method in which proteins are extracted from isolated microorganisms directly on a MALDI plate using concentrated formic acid in an organic solvent.

Referring to FIG. 3, which illustrates the protein extraction method of one embodiment of the disclosed methods, an isolated microorganism 300 is obtained (i.e. pure culture from sub-culturing or liquid separation as described in FIG. 1). The isolated microorganism 300 is resuspended in organic solvent 305 to produce resuspended microorganism 310. The isolated microorganism 300 can be resuspended in any suitable organic solvent 305 such as, for example, ethanol, methanol, acetone, or ethyl acetate. Any concentration of organic solvent 305 may be used, and the appropriate concentration for a particular application is readily determined by one skilled in the art. In alternative embodiments, the concentration of organic solvent 305 is in the range of about 30% to about 70%. In another alternative embodiment, the organic solvent is ethanol. The resuspended microorganism 310 is deposited onto a MALDI plate 315. The resuspended microorganism 310 on MALDI plate 315 is allowed to air dry 320 to produce dried, isolated microorganism 325. Seventy percent formic acid in 30% organic solvent 330 is used to extract the dried, isolated microorganism 325. The dried, isolated microorganism 325 on MALDI plate 315 with 70% formic acid in 30% organic solvent 330 is allowed to air dry 335 to produce dried, extracted microorganism 340. MALDI matrix 345 is added to dried, extracted microorganism 340 and allowed to air dry 350 before identification by MALDI-MS 355.

The isolated microorganism 300 is obtained according to any of the exemplary methods described herein or by other methods known to one having ordinary skill in the art.

In one embodiment, the microorganism is identified by: i) obtaining a sample suspected of containing at least one microorganism; ii) resuspending the sample in an organic solvent; iii) depositing at least a portion of the suspension on a solid surface adapted to be placed in an apparatus configured to determine the identity of microorganisms by MALDI mass spectrometry; iv) drying the sample; v) treating the sample with formic acid; vi) drying the sample; vii) placing a MALDI matrix solution over the treated sample; viii) drying the sample; and ix) identifying the microorganism by mass spectrometry. In this embodiment, the sample suspected of containing at least one microorganism is resuspended in an organic solution at a concentration greater than 0.5 McFarland. On one embodiment, the concentration of formic acid is at least 70%. In another embodiment, a kit is provided comprising one or more of the reagents and/or buffers described herein for processing a sample known to contain at least one microorganism for downstream identification.

In another embodiment, the microorganism is identified by: i) obtaining a sample suspected of containing at least one microorganism; ii) resuspending the sample in water; iii) depositing at least a portion of the suspension on a solid surface adapted to be placed in an apparatus configured to determine the identity of microorganisms by MALDI mass spectrometry; iv) drying the sample; v) treating the sample with formic acid and an organic solvent; vi) drying the sample; vii) placing a MALDI matrix solution over the treated sample; viii) drying the sample; and ix) identifying the microorganism by mass spectrometry. In this embodiment, the sample suspected of containing at least one microorganism is resuspended in an aqueous solution at a concentration greater than 0.5 McFarland. In another embodiment, a kit is provided comprising one or more of the reagents and/or buffers described herein for processing a sample known to contain at least one microorganism for downstream identification.

In another embodiment, the microorganism is identified by: i) obtaining a sample suspected of containing at least one microorganism; ii) resuspending the sample in an organic solvent solution; iii) depositing at least a portion of the suspension on a solid surface adapted to be placed in an apparatus configured to determine the identity of microorganisms by MALDI mass spectrometry; iv) drying the sample; v) treating the sample with formic acid in the organic solvent; vi) drying the sample; vii) placing a MALDI matrix solution over the treated sample; viii) drying the sample; and ix) identifying the microorganism by mass spectrometry. In this embodiment, the sample suspected of containing at least one microorganism is resuspended in an organic solvent solution at a concentration greater than 0.5 McFarland. In one embodiment, the sample is resuspended in organic solvent solution with an organic solvent concentration of about 30% to about 70%. In another embodiment, the organic solvent is ethanol. In yet another embodiment, the microorganism to be detected is yeast. In another embodiment, a kit is provided comprising one or more of the reagents and/or buffers described herein for processing a sample known to contain at least one microorganism for downstream identification.

In another embodiment, the microorganism is identified by: i) obtaining a sample suspected of containing at least one microorganism; ii) resuspending the sample in water; iii) combining the microorganism resuspended in water with an organic solvent so that the final concentration of organic solvent in the combined solution is in the range of 30%-70%; iv) depositing at least a portion of the suspension on a solid surface adapted to be placed in an apparatus configured to determine the identity of microorganisms by MALDI mass spectrometry; v) drying the sample; vi) treating the sample with an aqueous formic acid solution or formic acid in the organic solvent; vii) drying the sample; viii) placing a MALDI matrix solution over the treated sample; ix) drying the sample; and x) identifying the microorganism by mass spectrometry. In this embodiment, the sample suspected of containing at least one microorganism is resuspended in water at a concentration greater than about 0.5 McFarland. In another embodiment, a kit is provided comprising one or more of the reagents and/or buffers described herein for processing a sample known to contain at least one microorganism for downstream identification.

In another embodiment, the microorganism is identified by: i) obtaining a sample suspected of containing at least one microorganism; ii) resuspending the sample in water; iii) depositing at least a portion of the suspension on a solid surface adapted to be placed in an apparatus configured to determine the identity of microorganisms by MALDI mass spectrometry; iv) drying the sample; v) treating the sample with an organic solvent; vi) drying the sample; vii) treating the sample with formic acid in the organic solvent; viii) drying the sample; ix) placing a MALDI matrix solution over the treated sample; x) drying the sample; and xi) identifying the microorganism by mass spectrometry. In this embodiment, the organic solvent is ethanol and the sample suspected of containing at least one microorganism is resuspended in water at a concentration greater than 0.5 McFarland. In another embodiment, a kit is provided comprising one or more of the reagents and/or buffers described herein for processing a sample known to contain at least one microorganism for downstream identification.

In yet another embodiment, the microorganism is identified by: i) obtaining a sample suspected of containing at least one microorganism; ii) depositing by direct smear or suspension at least a portion of the sample on a solid surface adapted to be placed in an apparatus configured to determine the identity of microorganisms by MALDI mass spectrometry; iii) treating the sample with a mixture of formic acid, an organic solvent such as ethanol or acetonitrile, and a MALDI matrix solution; iv) drying the sample; and v) identifying the microorganism by mass spectrometry. In another embodiment, a kit is provided comprising one or more of the reagents and/or buffers described herein for processing a sample known to contain at least one microorganism for downstream identification.

In another embodiment, the microorganism is identified by: i) obtaining a sample suspected of containing at least one microorganism; ii) depositing at least a portion of the sample on a solid surface adapted to be placed in an apparatus configured to determine the identity of microorganisms by MALDI mass spectrometry; iii) drying the sample; iv) treating the sample with an organic solvent solution that is at least about 70% organic solvent; v) drying the sample; vi) treating the sample with a formic acid solution that is at least about 70% formic acid; vii) drying the sample; viii) treating the sample with concentrated (100%) organic solvent; ix) drying the sample, x) placing a MALDI matrix solution over the treated sample; xi) drying the sample; and xii) identifying the microorganism by mass spectrometry. In one embodiment, the organic solvent is ethanol. In another embodiment, a kit is provided comprising one or more of the reagents and/or buffers described herein for processing a sample known to contain at least one microorganism for downstream identification.

In an alternative embodiment, the microorganism is identified by: i) obtaining a sample suspected of containing at least one microorganism; ii) depositing, via direct smear or from a microbial suspension, at least a portion of the sample on a solid surface adapted to be placed in an apparatus configured to determine the identity of microorganisms by MALDI mass spectrometry; iii) fixing the microorganism with an organic solvent, e.g. ethanol, a fixative, e.g. formaldehyde, or by applying heat, generally up to about 37° C. (i.e. approximately body temperature); iv) treating the fixed sample with at least 70% formic acid; v) drying the sample; vi) placing a MALDI matrix solution over the treated sample; vii) drying the sample; and viii) identifying the microorganism by mass spectrometry. Fixatives such as formaldehyde are well known to one skilled in the art and are not described in detail herein. In another embodiment, a kit is provided comprising one or more of the reagents and/or buffers described herein for processing a sample known to contain at least one microorganism for downstream identification.

EXAMPLES

In all examples below, the MALDI matrix solution was prepared by dissolving 2.5 mg of HCCA in 250 µL of a solution that is 2.5% trifluoroacetic acid, 47.5% deionized water, and 50% acetonitrile. All the mass spectrometry data was recorded on Bruker Microflex LT with Biotyper software with the following MALDI score key definition. A MALDI ID score of greater than 2.0 indicates a satisfactory identification to the Genus and Species level. A MALDI ID score of 1.7-1.999 indicates a satisfactory identification to the Genus level. A MALDI ID score of less than 1.699 indicates an unacceptable or not reliable identification.

Example 1

Comparison of Extraction Methods

Prior Art Procedure:

The method and results from this prior art procedure are reported in and describe the findings of Haigh et al. "Improved Performance of Bacterium and Yeast Identification by a Commercial Matrix-Assisted Laser Desorption Ionisation-Time of Flight Mass Spectrometry System in the Clinical Microbiology Laboratory", *J. Clin. Microbiol.* (Jul. 6, 2011) and Bizzini et al. "Performance of Matrix-Assisted Laser Desorption Ionization-Time of Flight Mass Spectrometry for Identification of Bacterial Strains Routinely Isolated in a Clinical Microbiology Laboratory", J. Clin. Microbiol. (Mar. 10, 2010). A portion of isolated microorganism(s), including gram-positive and gram-negative bacteria, is directly smeared onto a MALDI-TOF MS plate and air dried. The dried sample is overlaid with 1 µL of matrix solution (HCCA) and air dried before identification by MALDI-TOF MS.

The MALDI analysis results in an overall correct identification of 70.3-75.6%. Therefore, at least 25% of the samples are not identified using this method (referred to as the "direct smear method").

For those samples not identified by the direct smear method above, a liquid extraction method is performed on the microorganism sample prior to identification. Water (300 µL) is added to an Eppendorf microcentrifuge tube. A large single colony from a sub-culture of the microorganism is transferred to the centrifuge tube containing water and the sample is vortexed thoroughly. Ethanol (900 µL) is added to the tube and vortexed thoroughly. The mixture is centrifuged at maximum speed for 2 minutes at 10,000×g in a microcentrifuge. The ethanol is decanted and the sample is centrifuged again for 2 minutes at 10,000×g speed in a microcentrifuge. Excess ethanol is removed with a pipette. Formic acid (70% solution; 50 µL) is added to the pellet and vortexed thoroughly. Acetonitrile (100% solution; 50 µL) is added to sample. The sample is centrifuged at 10,000×g for 2 minutes in a microcentrifuge. The supernatant (1 µL) is pipetted onto a MALDI plate and allowed to air dry. The dried sample is overlaid with 1 µL of MALDI matrix solution (HCCA) and air dried before identification by MALDI-MS. The liquid extraction procedure results in up to 100% identification of those microorganisms not identified by the direct smear method.

Exemplary Embodiment

From a PBC sample, the pellet of isolated microorganisms was resuspended in 600 µL water or 2 mM OG solution in a microcentrifuge tube. The turbidity was visually adjusted to greater than 0.5 McFarland. Each sample (1-1.5 µL) was spotted onto the MALDI plate. The sample was allowed to air dry. Formic acid (1-2 µL of 70% formic acid solution) was overlaid onto the dried, spotted sample and allowed to air dry. The dried sample was overlaid with 1 µl of matrix solution (HCCA) and allowed to air dry before identification by MALDI-TOF MS.

From a sub-culture, a single colony was touched with a toothpick and a very thin layer of microorganism was smeared directly onto MALDI target plate. The sample was allowed to air dry. Formic acid (1-2 µL of a 70% aqueous solution) was overlaid onto the sample and allowed to air dry. The dried sample was overlaid with 1 µl of MALDI matrix solution (HCCA) and allowed to air dry before identification by MALDI-MS.

The list of organisms tested can be found in Table 1 below. The MALDI-TOF MS analysis from both the microorganism isolated from a PBC sample and from a sub-culture resulted in 95% correct identification, including 95% identification of gram-positive bacteria (organism and type), 100% identification of gram-negative (organism and type), and 100% identification of yeast samples. These results illustrate that the methods described in this example can accurately identify microorganism(s) from a PBC sample or from a sub-culture without the need for the complex and time-consuming prior art liquid extraction methods previously described. Specifically, no separate extraction step was required to identify microorganisms not identified by the methods in this example. In addition, the results demonstrate that these methods result in significantly higher percent identification of a variety of organisms including gram-positive bacteria and gram-negative bacteria, compared to the direct smear method.

TABLE 1

| Organism | Organism Type | Strain Number |
| --- | --- | --- |
| *Acinetobacter baumanii* | gram-negative | ENF 11091 |
| *Enterobacter aerogenes* | gram-negative | 13048 |
| *Enterobacter cloacae* | gram-negative | 35030 |
| *Escherichia coli* | gram-negative | 25922 |
| *Escherichia coli* | gram-negative | 35218 |

TABLE 1-continued

| Organism | Organism Type | Strain Number |
|---|---|---|
| Klebsiella pneumoniae | gram-negative | 33495 |
| Klebsiella pneumoniae (ESBL-producer) | gram-negative | 700603 |
| Proteus mirabilis | gram-negative | 29906 |
| Pseudomonas aeruginosa | gram-negative | 27853 |
| Pseudomonas aeruginosa (Carbap-R) | gram-negative | ENF 14620 |
| Serratia marcescens | gram-negative | SCENF FR197 |
| Stenotrophomonas maltophilia | gram-negative | 13637 |
| Enterococcus faecalis | gram-positive | 29212 |
| Enterococcus faecalis VRE | gram-positive | 51299 |
| Enterococcus faecium | gram-positive | 19434 |
| Enterococcus faecium VRE | gram-positive | 700221 |
| Staphylococcus aureus | gram-positive | 25923 |
| Staphylococcus aureus | gram-positive | 29213 |
| Staphylococcus aureus MRSA | gram-positive | POS 3421 |
| Staphylococcus aureus MRSA | gram-positive | 43300 |
| Staphylococcus epidermidis | gram-positive | SCPOS 3568 |
| Staphylococcus epidermidis | gram-positive | 14990 |
| Staphylococcus haemolyticus | gram-positive | POS 3569 |
| Staphylococcus sciuri | gram-positive | 29062 |
| Streptococcus agalactiae | gram-positive | 12386 |
| Streptococcus agalactiae | gram-positive | 13813 |
| Streptococcus pneumoniae | gram-positive | 49619 |
| Streptococcus pneumoniae | gram-positive | 6303 |
| Streptococcus pneumoniae (P-resistant) | gram-positive | 700670 |
| Streptococcus pyogenes | gram-positive | 19615 |
| Viridans Streptococci (Strep salivarius) | gram-positive | POS 3177 |
| Viridans Streptococci (Strep mitis) | gram-positive | 49456 |
| Candida albicans | yeast | 18804 |
| Candida albicans | yeast | 24433 |
| Candida glabrata | yeast | 2001 |
| Candida parapsilosis | yeast | 22019 |

Example 2

Comparison of Extraction Protocols

Prior Art Procedure:

A liquid sample (0.5 µL) was applied to a target plate and covered with 0.5 µL of formic acid (FA: 25%; AnagnosTec) and allowed to air dry. Therefore, the total formic acid concentration was 12.5%. The dried sample was overlaid with 0.5 µL of 20 mg 2, 5-dihydroxybenzoic acid (DHB; AnagnosTec). The matrix sample was crystallized by air drying at room temperature for 5 minutes. Measurements were performed with a Shimadzu Biotech AXIMA Assurance™ mass spectrometer equipped with a 337-nm nitrogen laser. This method correctly identified 60% of gram-positive bacteria and 86.6% gram-negative bacteria. The method and results of this example summarize the findings of Schmidt et al., "Rapid identification of bacteria in positive blood culture by matrix-assisted laser desorption ionization time-of-flight mass spectrometry," Eur. J. Clin. Microbiol Infect Dis, 23 Jun. 2011.

Exemplary Embodiment

The pellet of isolated microorganism from a PBC sample was resuspended in 600 µL water or 2 mM OG solution in a microcentrifuge tube. The turbidity was visually adjusted to greater than 0.5 McFarland. Sample (1-1.5 µL) was spotted onto the MALDI plate. The sample was allowed to air dry. Formic acid (1-2 µL of a 70% solution) was overlaid onto the sample and allowed to air dry. The dried sample was overlaid with 1 µL of matrix solution (HCCA) and allowed to air dry before identification by MALDI-TOF MS. This method correctly identified 95% of gram-positive bacteria and 100% gram-negative bacteria. These results illustrate that the use of formic acid at a concentration well above 12.5% significantly increases the rate of identification of both gram-positive and gram-negative bacteria.

Example 3

Comparison of Extraction Methods with Various Yeast Strains

Prior Art Method:

Yeast colonies were resuspended in 600 µl of water in a microcentrifuge tube. The turbidity of the sample was visually adjusted to greater than 2.0 McFarland. Sample (0.5 µL) was pipetted onto a MALDI plate. Formic acid (0.5 µL of a 25% solution in water) was pipetted onto the sample and allowed to air dry. Therefore, the final concentration of formic acid was 12.5%. Matrix solution (1 µL HCCA) was overlaid onto the dried sample and allowed to air dry before identification by MALDI-TOF MS. This prior art method is the same method as disclosed in Schmidt et al., Rapid identification of bacteria in positive blood culture by matrix-assisted laser desorption ionization time-of-flight mass spectrometry, Eur. J. Clin. Microbiol. Infect Dis, 23 Jun. 2011.

Exemplary Control Method 1

Yeast colonies were resuspended in 600 µl of water in a microcentrifuge tube. The turbidity of the sample was visually adjusted to greater than 2.0 McFarland. Sample (1 µL) was pipetted onto a MALDI plate and allowed to air dry. Formic acid (1 µL of a 50% solution in water) was pipetted onto the dried sample and allowed to air dry. MALDI matrix solution (1 µL of HCCA) was pipetted onto the dried sample and allowed to air dry before identification by MALDI-MS.

Exemplary Control Method 2

Yeast colonies were resuspended in 600 µL of water in a microcentrifuge tube. The turbidity of the sample was visually adjusted to greater than 4.0 McFarland. Sample (1-1.5 µL) was pipetted onto a MALDI plate and allowed to air dry. No formic acid extraction was performed; rather the dried sample was directly overlaid with matrix solution (1 µL of HCCA) and allowed to air dry before identification by MALDI-TOF MS.

Exemplary Embodiment

Yeast colonies were resuspended in 600 µL of water in a microcentrifuge tube. The turbidity of the sample was visually adjusted to greater than 4.0 McFarland. Sample (1-1.5 µL) was pipetted onto a MALDI plate and allowed to air dry. Formic acid (1-1.5 µL of a 60%, 70%, or 90% solution of formic acid in water) was pipetted onto the dried sample and allowed to air dry. Matrix solution (1 µL of HCCA) was overlaid onto the dried sample and allowed to air dry before identification by MALDI-TOF MS.

The results are summarized in Table 2 below and indicate a positive identification, "Yes", or a failed identification, "No", by MALDI-TOF MS. The results illustrate that the on-plate extraction methods described herein, when used with at least 70% formic acid, are sufficient to identify various yeast strains. In contrast, the prior art and control methods, which utilize 50% or less formic acid, failed to identify any of the yeast strains.

TABLE 2

| Organism | Strain Number | No Formic Acid Extraction | 12.5% Formic Acid (Prior Art Method) | 50% Formic Acid (Control Method 1) | 60% Formic Acid (Control Method 2) | 70% Formic Acid | 90% Formic Acid |
|---|---|---|---|---|---|---|---|
| Candida albicans | ATCC 145 | No | No | No | No | Yes | Yes |
| Candida parapsilosis | ATCC 147 | No | No | No | No | Yes | Yes |
| Candida glabrata | ATCC 394 | No | No | No | No | Yes | Yes |

Example 4

Comparison of Exemplary Extraction Protocols with 90% Formic Acid+/−Ethyl Acetate for the Identification of Various Yeast Strains

Exemplary Embodiment

Yeast colonies were resuspended in 600 µL of water in a microcentrifuge tube. The turbidity of the sample was visually adjusted to greater than 2.0 McFarland. Duplicate samples (1-1.5 µL each) were pipetted onto a MALDI-TOF MS plate and allowed to air dry. Formic acid (1-1.5 µL) of either a 90% solution in water or a 90% solution in ethyl acetate was pipetted onto the dried samples and allowed to air dry. Matrix solution (1 µL HCCA) was overlaid onto the dried samples and allowed to air dry before identification by MALDI-TOF MS. In all, four samples (two samples for each formic acid solution) for each organism were prepared and subjected to MALDI-TOF MS analysis The MALDI score results are summarized in Table 3 below. These results illustrate an improved identification performance when formic acid extraction buffer is prepared in an organic solvent, for example, ethyl acetate, compared to formic acid in an aqueous solution.

TABLE 3

| Organism | Strain Number | 90% Formic Acid in Water | 90% Formic Acid in Ethyl Acetate |
|---|---|---|---|
| Candida glabrata | YST 26 | 2.098 | 2.123 |
| | | 2.211 | 2.038 |
| Cryptococcus neoformans | YST 54 | 1.579 | 1.494 |
| | | 1.425 | 1.573 |
| Candida parapsilosis | YST 194 | 1.626 | 2.006 |
| | | 1.826 | 2.014 |
| Candida parapsilosis | YST 792 | 1.766 | 1.856 |
| | | 1.532 | 1.805 |
| Cryptococcus neoformans | YST 1162 | 1.437 | 1.561 |
| | | 1.481 | 1.741 |
| Candida albicans | YST 1235 | 1.754 | 1.837 |
| | | 1.656 | 1.813 |
| Cryptococcus | YST | 1.344 | 1.386 |

TABLE 3-continued

| Organism | Strain Number | 90% Formic Acid in Water | 90% Formic Acid in Ethyl Acetate |
|---|---|---|---|
| neoformans | 1479 | 1.436 | 1.442 |
| Cryptococcus neoformans | YST 1481 | 1.552 | 1.617 |
| | | 1.693 | 1.772 |

Example 5

Comparison of Exemplary Extraction Protocols with Formic Acid+/−Acetonitrile or Formic Acid+/−OG Buffer for the Identification of Various Yeast Strains

Exemplary Embodiment

Yeast colonies were resuspended in 600 µL of water in a microcentrifuge tube. The turbidity of the sample was visually adjusted to greater than 4.0 McFarland. Duplicate samples (1-1.5 µL) were pipetted onto a MALDI-TOF MS plate and allowed to air dry. Various formic acid extraction buffers were prepared including: 70% formic acid in water; 90% formic acid in water; 70% formic acid in 20 mM OG buffer in water; and, 90% formic acid in 20 mM OG buffer in water. A volume of the extraction buffer (1-1.5 µL) was pipetted onto the dried samples and allowed to air dry. In one set of samples treated with 90% formic acid in water, a subsequent extraction step was performed by overlaying the dried sample with 50% acetonitrile in water and allowing the sample to air dry. Matrix solution (1 µL of HCCA) was overlaid onto the dried samples and allowed to air dry before identification by MALDI-TOF MS. A total of eight samples were prepared for each organism (two for each extraction buffer) and evaluated by MALDI-TOF MS.

The MALDI-TOF MS score results are summarized in Table 4 below. The results illustrate that even microorganisms that are often difficult to identify, such as yeast, can be reliably identified by using an extraction buffer containing 90% formic acid, by preparing the formic acid extraction buffer in OG buffer or by performing a subsequent solvent only extraction step using an organic solvent such as acetonitrile.

TABLE 4

| Organism | Strain Number | 70% formic acid in water | 90% formic acid in water | 90% formic acid in water followed by 50% acetonitrile in water | 70% formic acid in 20 mM OG buffer in water | 90% formic acid in 20 mM OG buffer in water |
|---|---|---|---|---|---|---|
| Candida glabrata | ATCC 2001 | 1.89 | 1.845 | 1.956 | 1.856 | 1.884 |
| | | 1.932 | 1.96 | 1.968 | 1.931 | 1.979 |
| Candida albicans | ATCC 18804 | 1.673 | 2.093 | 1.932 | 2.016 | 2.019 |
| | | 1.643 | 1.927 | 2.009 | 1.998 | 2.093 |

TABLE 4-continued

| Organism | Strain Number | 70% formic acid in water | 90% formic acid in water | 90% formic acid in water followed by 50% acetonitrile in water | 70% formic acid in 20 mM OG buffer in water | 90% formic acid in 20 mM OG buffer in water |
|---|---|---|---|---|---|---|
| Candida parapsilosis | ATCC 22019 | <0 | 1.718 | 1.642 | 1.787 | 2.036 |
|  |  | <0 | 2.131 | 1.861 | 1.871 | 1.976 |
| Candida albicans | ATCC 24433 | 1.58 | 1.687 | 1.874 | 1.684 | 2.06 |
|  |  | 1.356 | 1.835 | 1.9 | 1.788 | 1.893 |
| Candida glabrata | BQ141 | 2.076 | 1.997 | 2.088 | 2.205 | 2.229 |
|  |  | 1.912 | 2.064 | 2.051 | 2.172 | 2.171 |
| Candida glabrata | BP154 | 1.941 | 1.845 | 1.996 | 2.154 | 2.165 |
|  |  | 1.867 | 2.034 | 2.181 | 1.977 | 2.199 |

Example 6

Identification of Various Bacteria According to One Embodiment

Exemplary Embodiment

Bacterial colonies from a sub-culture were resuspended in 600 µL water. The turbidity of the sample was visually adjusted to greater than 4.0 McFarland. Three aliquots of the bacterial suspension (1.5 µL) for each microorganism were spotted onto a MALDI-TOF MS plate, and then immediately followed by sequential additions of 1.5 µL of 70% formic acid in ethanol and 1.5 µL of matrix solution (HCCA). The samples were allowed to air dry before identification by MALDI-TOF MS. The same experiment was repeated on a subsequent day by preparing a second bacterial suspension for each microorganism and performing the extraction procedure again preparing three samples for each microorganism.

The MALDI-TOF MS score results are summarized in Table 5 below. These results illustrate that drying the sample after applying the extraction buffer and before applying the matrix solution is not required to obtain positive identification of the microorganism. In addition, these results demonstrate the reproducibility of the extraction procedure. Specifically, overall, two different sample suspensions produce substantially similar identification results.

TABLE 5

| Organism | Strain Number | Suspension 1 | Suspension 2 |
|---|---|---|---|
| Escherichia coli | 25922 | 2.292 | 2.140 |
|  |  | 2.260 | 2.254 |
|  |  | 2.207 | 2.246 |
| Enterococcus faecalis | 29212 | 2.445 | 2.567 |
|  |  | 2.385 | 2.565 |
|  |  | 2.263 | 2.524 |
| Staphylococcus haemolyticus | 3569 | 2.275 | 2.194 |
|  |  | 2.098 | 2.181 |
|  |  | 2.005 | 2.227 |
| Enterococcus faecium | 700221 | 2.316 | 2.482 |
|  |  | 2.377 | 2.444 |
|  |  | 0.000* | 2.320 |
| Staphylococcus haemolyticus | 2885 | 1.253 | 1.931 |
|  |  | 1.638 | 2.010 |
|  |  | 1.532 | 1.939 |
| Streptococcus agalactiae | 13813 | 2.276 | 2.527 |
|  |  | 2.320 | 2.419 |
|  |  | 2.196 | 2.442 |

TABLE 5-continued

| Organism | Strain Number | Suspension 1 | Suspension 2 |
|---|---|---|---|
| Streptococcus pneumoniae | 49456 | 2.154 | 2.196 |
|  |  | 2.286 | 2.191 |
|  |  | 2.157 | 2.138 |
| Klebsiella pneumoniae | 700603 | 2.189 | 0.000* |
|  |  | 2.054 | 2.006 |
|  |  | 2.126 | 2.057 |

*These results are considered anomalies in the overall context of the data, and not viewed as a failure in the extraction protocol.

Example 7

Exemplary Embodiments of the Disclosed Methods Compared to Control Methods for the Identification of Yeast Strains Exemplary Control Method (Process 22)

Yeast colonies were resuspended in 600 µL of water in a microcentrifuge tube. The turbidity of the sample was visually adjusted to greater than 2.0 McFarland. Three samples (1 µL) for each microorganism were pipetted onto a MALDI-TOF MS plate and allowed to air dry. Neat formic acid (1 µL) was pipetted onto the dried samples and allowed to air dry. Matrix solution (1 µL of HCCA) was overlaid onto the dried samples and allowed to air dry before identification by MALDI-TOF MS.

Exemplary Embodiment

On Plate Extraction from Ethanol Suspension (Process 18)

Yeast colonies from a sub-culture were resuspended in 600 µL of 50% ethanol in a microcentrifuge tube. The turbidity of the sample was visually adjusted to greater than 4.0 McFarland. Three samples (1 µL) for each microorganism were pipetted onto a MALDI-TOF MS plate and allowed to air dry. Formic acid (1 µL of 70% solution in ethanol) was pipetted onto the dried samples and allowed to air dry. Matrix solution (1 µL of HCCA) was overlaid onto the dried samples and allowed to air dry before identification by MALDI-TOF MS.

Exemplary Embodiment

On Plate Extraction from Water Suspension Followed by Ethanol (Process 19)

Yeast colonies from a sub-culture were resuspended in 600 µL of water in a microcentrifuge tube. The turbidity of the sample was visually adjusted to greater than 4.0 McFarland. Three samples (1 μL) for each microorganism were pipetted onto a MALDI plate and allowed to air dry. Ethanol (1 μL of 70% concentration) was pipetted onto the dried samples and allowed to air dry. A solution of 70% formic acid/30% ethanol was pipetted (1 μL) onto the dried samples and allowed to air dry. Matrix solution (1 μL of HCCA) was overlaid onto the dried samples and allowed to air dry before identification by MALDI-TOF MS.

Exemplary Embodiment

On Plate Extraction from Acetone Suspension (Process 23)

Yeast colonies from a sub-culture were resuspended in 600 μL of 50% acetone in a microcentrifuge tube. The turbidity of the sample was visually adjusted to greater than 4.0 McFarland. Three samples (1 μL) for each microorganism were pipetted onto a MALDI-TOF MS plate and allowed to air dry. Formic acid (1 μL of 70% concentration in acetone) was pipetted onto the dried samples and allowed to air dry. Matrix solution (1 μL of HCCA) was overlaid onto the dried samples and allowed to air dry before identification by MALDI-TOF MS.

Exemplary Embodiment

On Plate Extraction from Water Suspension Followed by Acetone (Process 24)

Yeast colonies from a sub-culture were resuspended in 600 μL of water in a microcentrifuge tube. The turbidity of the sample was visually adjusted to greater than 4.0 McFarland. Three samples (1 μL) for each microorganism were pipetted onto a MALDI-TOF MS plate and allowed to air dry. Acetone (1 μL of 70% concentration) was pipetted onto the dried samples and allowed to air dry. Formic acid (1 μl of 70% formic acid in acetone) was pipetted onto the dried samples and allowed to air dry. Matrix solution (1 μL HCCA) was overlaid onto the dried samples and allowed to air dry before identification by MALDI-MS.

The MALDI-TOF MS score results for each of the methods in this example are summarized in Table 6 below. The results illustrate that 70% formic acid with an organic solvent produces superior results than with neat formic acid alone for the identification of yeast strains independent of the suspension used. The type of organic solvent used with formic acid did not affect the overall results. In addition, the organic solvent can be added during suspension of the sample, prior to treatment with formic acid, and/or during formic acid treatment without decreasing the rate of identification of various yeast strains.

TABLE 6

| Oganism | Strain Number | Process 22 | Process 18 | Process 19 | Process 23 | Process 24 |
|---|---|---|---|---|---|---|
| Candida glabrata | YST 26 | 1.693 | 2.060 | 2.067 | 2.145 | 2.022 |
| | | 1.752 | 2.095 | 2.137 | 2.167 | 1.913 |
| | | 1.766 | 2.097 | 2.129 | 2.172 | 1.898 |
| Cryptococcus neoformans | YST 54 | 1.823 | 1.870 | 1.826 | 1.862 | 1.525 |
| | | 1.794 | 0.000 | 1.990 | 1.917 | 1.282 |
| | | 1.918 | 1.816 | 1.872 | 1.902 | 0.000 |
| Candida parapsilosis | YST 194 | 1.927 | 1.842 | 1.949 | 1.942 | 1.814 |
| | | 1.968 | 1.881 | 2.093 | 2.007 | 1.864 |
| | | 2.053 | 1.974 | 2.105 | 1.926 | 1.860 |

TABLE 6-continued

| Oganism | Strain Number | Process 22 | Process 18 | Process 19 | Process 23 | Process 24 |
|---|---|---|---|---|---|---|
| Candida parapsilosis | YST 792 | 1.399 | 1.784 | 1.743 | 1.763 | 1.650 |
| | | 1.255 | 1.871 | 1.771 | 1.932 | 1.706 |
| | | 1.645 | 1.733 | 1.835 | 1.836 | 1.769 |
| Cryptococcus neoformans | YST 1162 | 1.325 | 1.550 | 1.681 | 1.815 | 1.591 |
| | | 1.489 | 1.776 | 1.657 | 1.671 | 1.431 |
| | | 1.504 | 1.623 | 1.741 | 1.566 | 1.562 |
| Candida albicans | YST 1235 | 1.148 | 2.072 | 2.024 | 1.744 | 1.968 |
| | | 1.460 | 2.065 | 2.004 | 1.700 | 1.960 |
| | | 1.365 | 2.037 | 1.987 | 1.837 | 1.981 |
| Cryptococcus neoformans | YST 1479 | 1.390 | 0.000 | 1.899 | 1.913 | 1.705 |
| | | 1.445 | 1.931 | 1.821 | 1.948 | 1.689 |
| | | 1.413 | 1.941 | 1.918 | 2.069 | 1.712 |
| Cryptococcus neoformans | YST 1481 | 1.299 | 0.000 | 2.071 | 2.020 | 1.860 |
| | | 1.315 | 2.139 | 2.076 | 1.905 | 1.824 |
| | | 1.485 | 2.022 | 2.093 | 1.981 | 1.799 |
| Candida albicans | YST 145 | 1.478 | 2.176 | 2.213 | 2.140 | 2.147 |
| | | 1.783 | 2.226 | 2.045 | 1.926 | 2.005 |
| | | 1.598 | 2.103 | 2.228 | 1.860 | 2.068 |
| Candida parapsilosis | YST 147 | 2.073 | 2.113 | 2.074 | 2.202 | 2.084 |
| | | 1.882 | 2.021 | 2.052 | 2.169 | 2.107 |
| | | 2.021 | 2.010 | 2.064 | 2.137 | 2.070 |
| Candida parapsilosis | YST 200 | 2.022 | 2.010 | 2.076 | 2.171 | 2.188 |
| | | 1.961 | 2.003 | 1.946 | 2.155 | 1.992 |
| | | 1.914 | 2.013 | 2.105 | 2.202 | 1.938 |
| Candida parapsilosis | YST 214 | 2.039 | 2.284 | 2.036 | 2.073 | 1.997 |
| | | 2.012 | 2.082 | 2.082 | 2.163 | 2.050 |
| | | 1.991 | 2.034 | 2.182 | 2.156 | 2.030 |
| Candida dubliniensis | YST 305 | 1.408 | 1.741 | 1.520 | 1.708 | 1.341 |
| | | 1.492 | 1.791 | 1.467 | 1.676 | 1.220 |
| | | 1.565 | 1.639 | 1.575 | 1.262 | 1.249 |
| Candida glabrata | YST 394 | 1.928 | 2.213 | 1.970 | 2.024 | 2.141 |
| | | 1.745 | 2.255 | 2.089 | 2.022 | 2.108 |
| | | 2.011 | 2.279 | 2.128 | 2.094 | 2.136 |
| Candida albicans | YST 1033 | 1.499 | 2.096 | 2.130 | 1.535 | 1.911 |
| | | 1.366 | 2.107 | 2.015 | 1.747 | 1.863 |
| | | 1.503 | 2.070 | 2.135 | 1.496 | 2.012 |
| Candida albicans | YST 1035 | 1.538 | 2.154 | 2.148 | 2.047 | 1.973 |
| | | 1.796 | 2.120 | 2.187 | 1.887 | 2.033 |
| | | 1.760 | 2.130 | 2.236 | 1.933 | 1.921 |
| Candida glabrata | YST 1045 | 2.029 | 2.276 | 2.278 | 2.251 | 2.219 |
| | | 1.904 | 2.286 | 2.179 | 2.232 | 2.175 |
| | | 1.986 | 2.247 | 2.297 | 2.253 | 2.145 |
| Cyptococcus neoformans | YST 1074 | 1.405 | 2.084 | 1.786 | 1.699 | 1.918 |
| | | 1.298 | 2.057 | 1.954 | 1.850 | 1.832 |
| | | 1.427 | 2.068 | 1.940 | 1.812 | 1.890 |
| Candida albicans | YST 1383 | 1.454 | 2.109 | 2.122 | 2.020 | 2.040 |
| | | 1.560 | 2.198 | 2.096 | 1.987 | 2.054 |
| | | 1.752 | 2.159 | 2.096 | 1.758 | 2.027 |
| Candida glab*rata | YST 1454 | 1.808 | 2.283 | 2.265 | 2.147 | 2.008 |
| | | 1.969 | 2.257 | 2.274 | 2.143 | 2.097 |
| | | 1.862 | 2.220 | 2.301 | 2.128 | 1.949 |

Example 8

Comparison of Exemplary Embodiments of the Disclosed Methods with Control Methods for the Identification of Yeast Strains Exemplary Control Yeast colonies from a pure culture plate were directly smeared onto a MALDI-TOF MS plate. Without drying, the matrix solution (1 μl of HCCA) was overlaid onto the sample and allowed to air dry before identification by MALDI-TOF MS.

Exemplary Embodiment

70% Formic Acid in Water

Yeast colonies from a pure culture plate were directly smeared onto a MALDI-TOF MS plate and allowed to air dry. Formic acid (1 μL of 70% formic acid solution in water) was pipetted onto the smear and allowed to air dry. Matrix solution (1 μL of HCCA) was overlaid onto the dried sample and allowed to air dry before identification by MALDI-TOF MS.

Exemplary Embodiment

70% Organic Solvent Followed by 70% Formic Acid in Water

Yeast colonies from a pure culture plate were directly smeared onto a MALDI-TOF MS plate and allowed to air dry. Organic solvent (1 μL of 70% solution in water) was pipetted onto the smear and allowed to air dry. The organic solvent was methanol, ethanol, isopropanol, or acetone. Formic acid (1 μL of 70% solution in water) was pipetted onto the dried sample and allowed to air dry. Matrix solution (1 μL of HCCA) was overlaid onto the dried sample and allowed to air dry before identification by MALDI-TOF MS.

The MALDI-TOF MS score results for each of the methods in this example are summarized in Table 7 below. The results indicate that for various yeast strains, using formic acid as an on-plate extraction solution provides a consistently higher rate of identification than the direct smear method without the use of formic acid. In addition, an additional extraction step with an organic solvent, prior to the formic acid on-plate extraction, results in a higher MALDI-TOF MS score than using the formic acid extraction alone.

which a microbial suspension is prepared by resuspending a microbial pellet in an organic solvent, for example, ethanol, followed by extraction with formic acid in ethanol provide 100% identification by MALDI-TOF MS for various yeast and bacteria strains.

TABLE 8

| Organism | Strain Number | MALDI-TOF MS Score |
|---|---|---|
| Candida glabrata | YST 26 | 2.013 |
|  |  | 2.184 |
|  |  | 2.189 |
| Cryptococcus neoformans | YST 54 | 1.856 |
|  |  | 2.068 |
|  |  | 1.912 |
| Candida parapsilosis | YST 194 | 1.929 |
|  |  | 1.957 |
|  |  | 2.113 |
| Candida parapsilosis | YST 792 | 1.962 |
|  |  | 1.831 |
|  |  | 1.844 |
| Cryptococcus neoformans | YST 1162 | 1.733 |
|  |  | 1.688 |
|  |  | 1.728 |
| Candida albicans | YST 1235 | 2.031 |
|  |  | 1.860 |
|  |  | 1.949 |
| Cryptococcus neoformans | YST 1479 | 1.966 |
|  |  | 1.974 |
|  |  | 1.966 |
| Cryptococcus neoformans | YST 1481 | 2.115 |
|  |  | 2.186 |
|  |  | 2.136 |

TABLE 7

| Organism | Strain Number | Direct Smear with no Formic Acid | Formic Acid Only | Methanol Followed by Formic Acid | Ethanol Followed by Formic Acid | Isopropanol Followed by Formic Acid | Acetone Followed by Formic Acid |
|---|---|---|---|---|---|---|---|
| Candida albicans | ATCC 18804 | 0 | 1.709 | 2.044 | 2.083 | 2.098 | 2.01 |
| Candida albicans | ATCC 24433 | 1.308 | 1.619 | 2.277 | 2.289 | 2.108 | 2.13 |
| Candida glabrata | ATCC 2001 | 1.329 | 1.889 | 2.128 | 2.209 | 2.18 | 2.172 |
| Candida parapsilosis | ATCC 22019 | 0 | 1.736 | 1.887 | 1.775 | 1.883 | 1.951 |
| Candida neoformans | ATCC 60234 | 0 | 1.421 | 1.779 | 1.886 | 1.83 | 1.949 |

Example 9

Identification of Various Yeast and Bacteria Strains Using Exemplary Extraction Methods with Formic Acid/Ethanol Solution Exemplary Embodiment Yeast or bacterial colonies were resuspended in water in a microcentrifuge tube. The turbidity of the sample was visually adjusted to greater than 4.0 McFarland. An aliquot of the suspension was diluted 1:1 with 95.5% ethanol. Three aliquots of the diluted suspension (1 μL) for each microorganism were pipetted onto a MALDI-TOF MS plate and allowed to air dry. Formic acid (1 μL of 70% solution in ethanol) was pipetted onto the dried samples and allowed to air dry. Matrix solution (1 μL of HCCA) was overlaid onto the dried samples and allowed to air dry before identification by MALDI-TOF MS.

The MALDI-TOF MS score results are summarized in Table 8 (yeast strains) and Table 9 (bacterial strains) below. Table 8 and 9 illustrate that on-plate extraction methods in TABLE 8-continued

| Organism | Strain Number | MALDI-TOF MS Score |
|---|---|---|
| Candida albicans | YST 145 | 2.176 |
|  |  | 2.226 |
|  |  | 2.103 |
| Candida parapsilosis | YST 147 | 2.113 |
|  |  | 2.021 |
|  |  | 2.010 |
| Candida parapsilosis | YST 200 | 2.010 |
|  |  | 2.003 |
|  |  | 2.013 |
| Candida parapsilosis | YST 214 | 2.284 |
|  |  | 2.082 |
|  |  | 2.034 |
| Candida dubliniensis | YST 305 | 1.741 |
|  |  | 1.791 |
|  |  | 1.639 |
| Candida glabrata | YST 394 | 2.213 |
|  |  | 2.255 |
|  |  | 2.279 |

TABLE 8-continued

| Organism | Strain Number | MALDI-TOF MS Score |
|---|---|---|
| Candida albicans | YST 1033 | 2.096 |
| | | 2.107 |
| | | 2.070 |
| Candida albicans | YST 1035 | 2.154 |
| | | 2.120 |
| | | 2.130 |
| Candida glabrata | YST 1045 | 2.276 |
| | | 2.286 |
| | | 2.247 |
| Cryptococcus neoformans | YST 1074 | 2.084 |
| | | 2.057 |
| | | 2.068 |
| Candida albicans | YST 1383 | 2.109 |
| | | 2.198 |
| | | 2.159 |
| Candida glabrata | YST 1454 | 2.283 |
| | | 2.257 |
| | | 2.220 |

TABLE 9

| Organism | Strain Number | MALDI-TOF MS score |
|---|---|---|
| Acinetobacter baumanii | ENF 11091 | 2.359 |
| | | 2.403 |
| | | 2.356 |
| Enterobacter aerogenes | 13048 | 2.410 |
| | | 2.409 |
| | | 2.427 |
| Enterobacter cloacae | 35030 | 2.178 |
| | | 2.097 |
| | | 2.042 |
| Escherichia coli | 25922 | 2.374 |
| | | 2.231 |
| | | 2.334 |
| Escherichia coli | 35213 | 2.387 |
| | | 2.164 |
| | | 2.219 |
| Klebsiella pneumoniae | 33495 | 2.282 |
| | | 2.335 |
| | | 2.351 |
| Klebsiella pneumoniae | 700603 | 2.200 |
| | | 2.046 |
| | | 2.190 |
| Proteus mirabilis | 29906 | 2.261 |
| | | 2.298 |
| | | 2.324 |
| Pseudomonas aeruginosa | 27853 | 2.276 |
| | | 2.367 |
| | | 2.325 |
| Pseudomonas aeruginosa | ENF 14620 | 2.258 |
| | | 2.275 |
| | | 1.999 |
| Serratia marcescens | FR197 | 2.139 |
| | | 2.081 |
| | | 2.054 |
| Stenotrophomonas maltophilia | 13637 | 2.128 |
| | | 1.784 |
| | | 2.139 |
| Enterococcus faecalis | 29212 | 2.318 |
| | | 2.216 |
| | | 2.269 |
| Enterococcus faecalis (VRE) | 51299 | 2.272 |
| | | 2.291 |
| | | 2.353 |
| Enterococcus faecium | 19434 | 2.373 |
| | | 2.389 |
| | | 2.271 |
| Enterococcus faecium VRE | 700221 | 1.862 |
| | | 1.977 |
| | | 1.894 |

TABLE 9-continued

| Organism | Strain Number | MALDI-TOF MS score |
|---|---|---|
| Staphylococcus aureus | 25923 | 2.379 |
| | | 2.285 |
| | | 2.391 |
| Staphylococcus aureus (MSSA) | 29213 | 2.331 |
| | | 2.305 |
| | | 2.387 |
| Staphylococcus aureus (MRSA) | 3421 | 2.324 |
| | | 2.323 |
| | | 2.370 |
| Staphylococcus aureus (MRSA) | 4330 | 2.245 |
| | | 2.187 |
| | | 2.200 |
| Staphylococcus epidermidis | 3568 | 1.953 |
| | | 1.777 |
| | | 1.861 |
| Staphylococcus epidermidis | 77 | 2.051 |
| | | 2.039 |
| | | 2.001 |
| Staphylococcus haemolyticus | 356 | 0.000 |
| | | 2.071 |
| | | 1.883 |
| Staphylococcus sciuri | 29062 | 1.910 |
| | | 1.751 |
| | | 1.865 |
| Streptococcus agalactiae | 12386 | 2.227 |
| | | 2.134 |
| | | 2.269 |
| Streptococcus agalactiae | 13813 | 2.229 |
| | | 2.189 |
| | | 2.304 |
| Streptococcus pneumoniae | 49619 | 2.143 |
| | | 1.923 |
| | | 2.067 |
| Streptococcus pneumoniae | 6303 | 2.124 |
| | | 2.001 |
| | | 2.019 |
| Streptococcus pneumoniae | 700670 | 2.058 |
| | | 2.321 |
| | | 2.185 |
| Streptococcus pyogenes | 19615 | 2.380 |
| | | 1.721 |
| | | 2.474 |
| Streptococcus salivarius | 3177 | 1.864 |
| | | 1.712 |
| | | 1.943 |
| Streptococcus mitis | 49456 | 2.119 |
| | | 2.021 |
| | | 1.995 |

The various embodiments described and illustrated herein, demonstrate various methods for identifying microorganism(s) in a sample resulting in a consistently superior rate of identification with fewer steps compared to the prior art methods. The on-plate extraction methods are easily amenable to automated procedures as there is no need for centrifugation. In addition, the extraction plate can be heated in order to increase the speed of the various drying steps resulting in a fast and accurate process for identifying microorganism(s) in a sample.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for characterizing at least one microorganism in a sample for identification of microorganisms therein, the method comprising:

(a) obtaining a sample containing at least one microorganism, wherein the sample is in a suspension;
(b) depositing at least a portion of the obtained sample on a solid surface adapted to be placed in an apparatus configured to determine the identity of microorganisms by mass spectrometry;
(c) drying the deposited sample;
(d) treating the deposited and dried sample with a volatile acid solution, wherein the volume percent of the volatile acid is at least 70% of the volatile acid solution combined with the sample, and the volatile acid solution is a volatile acid in water or a volatile solution in an organic solvent;
(e) drying the treated sample;
(f) placing a matrix over the treated and dried sample; and
(g) identifying the microorganisms by a mass spectrometry.

2. The method of claim 1, wherein the suspension is in a solution selected from the group consisting of water, an organic solvent, and combinations thereof.

3. The method of claim 1, wherein the volatile acid solution is formic acid in water at a volume percent of 70% when combined with the sample.

4. The method of claim 1, wherein the volatile acid solution is formic acid in water at a volume percent of about 80% when combined with the sample.

5. The method of claim 1, wherein the volatile acid solution is formic acid in water at a volume percent of about 90% when combined with the sample.

6. The method of claim 1, wherein the organic solvent is selected from the group consisting of ethanol, methanol, isopropanol, acetonitrile, acetone, and ethyl acetate.

7. The method of claim 1, further comprising using a non-ionic detergent, wherein the detergent can be used during the steps selected from the group consisting of obtaining the sample, treating the sample with the volatile acid solution, and combinations thereof.

8. The method of claim 1, further comprising:
(i) treating the deposited and dried sample from step (c) with an organic solvent;
and drying the treated sample before step (d);
and
(ii) drying the sample containing matrix from step (f) before step (g).

9. The method of claim 1, further comprising:
(i) drying the treated sample from step (d); and treating the dried sample with an organic solvent before step (e);
and
(ii) drying the sample containing matrix before step (g).

10. The method of claim 2, wherein the concentration of the microbial suspension is at least about 0.5 McFarland.

11. The method of claim 1, further comprising:
drying the sample containing matrix from step (f) before step (g), wherein the volatile acid is formic acid.

12. A method for preparing a positive blood culture sample for identification of microorganisms therein, the method comprising:
(a) obtaining a positive blood culture sample determined to contain at least one microorganism;
(b) adding a lysis buffer to the obtained sample, wherein the lysis buffer is selected to lyse the blood cells in the sample while the microorganism remains intact;
(c) concentrating the microorganisms in the sample containing lysis buffer, wherein the concentrated sample is a suspension;
(d) separating the concentrated portion of the sample in the suspension from the remainder;
(e) depositing at least a portion of the separated microbial sample in the suspension on a surface adapted to be placed in an apparatus configured to determine the identity of a microorganism by mass spectrometry;
(f) drying the deposited sample;
(g) treating the deposited and dried sample with a volatile acid solution, wherein the volume percent of the volatile acid is at least 70% of the volatile acid solution combined with the sample, and the volatile acid solution is a volatile acid in an organic solvent;
(h) drying the treated sample;
(i) placing a matrix over the treated and dried sample; and
(j) drying the sample.

* * * * *